United States Patent
Andreas et al.

(10) Patent No.: US 7,357,812 B2
(45) Date of Patent: *Apr. 15, 2008

(54) APPARATUS AND METHODS FOR DELIVERY OF BRAIDED PROSTHESES

(75) Inventors: Bernard Andreas, Redwood City, CA (US); Ron French, Santa Clara, CA (US); Mark E. Deem, Mountain View, CA (US); Hanson S. Gifford, III, Woodside, CA (US); Alan Will, Atherton, CA (US)

(73) Assignee: Xtent, Inc., Menlo Park, CA (US)

( * ) Notice: Subject to any disclaimer, the term of this patent is extended or adjusted under 35 U.S.C. 154(b) by 439 days.

This patent is subject to a terminal disclaimer.

(21) Appl. No.: 10/966,806

(22) Filed: Oct. 14, 2004

(65) Prior Publication Data
US 2005/0049673 A1 Mar. 3, 2005

Related U.S. Application Data

(63) Continuation of application No. 10/306,620, filed on Nov. 27, 2002, now Pat. No. 7,147,656.

(60) Provisional application No. 60/336,607, filed on Dec. 3, 2001.

(51) Int. Cl.
*A61F 2/06* (2006.01)
(52) U.S. Cl. .................... 623/1.11; 623/903
(58) Field of Classification Search ...... 623/1.11–1.36; 604/508
See application file for complete search history.

(56) References Cited

U.S. PATENT DOCUMENTS

| | | | |
|---|---|---|---|
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,733,665 A | 3/1988 | Palmz |

(Continued)

FOREIGN PATENT DOCUMENTS

EP 203945 B2 12/1986

(Continued)

OTHER PUBLICATIONS

Colombo, "The Invatec Bifurcation Stent Solution"Bifurcation Stents: Novel Solutions, TCT 2003, Washington: Sep. 15-19, 2003, 24 pages total.

(Continued)

*Primary Examiner*—Suzette Gherbi
(74) *Attorney, Agent, or Firm*—Townsend and Townsend and Crew LLP; J Grainger, Esq.

(57) ABSTRACT

Blood vessels and other body lumens are expanded using an evertible braided prosthesis. The braided prosthesis is delivered to the blood vessel in a radially collapsed configuration. A leading edge of the braided prosthesis is then everted so that it expands as it is advanced through the blood vessel. Optionally, the prosthesis can be provided with a biologically active substance in order to inhibit hyperplasia or have other desired biological effects.

18 Claims, 2 Drawing Sheets

U.S. PATENT DOCUMENTS

| | | |
|---|---|---|
| 4,739,762 A | 4/1988 | Palmz |
| 4,762,129 A | 8/1988 | Bonzel |
| 4,775,337 A | 10/1988 | Van Wagener et al. |
| 4,776,337 A | 10/1988 | Palmaz |
| 4,886,062 A | 12/1989 | Wiktor |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,040,548 A | 8/1991 | Yock |
| 5,092,877 A | 3/1992 | Pinchuk |
| 5,102,417 A | 4/1992 | Palmz |
| 5,104,404 A | 4/1992 | Wolff |
| 5,135,535 A | 8/1992 | Kramer |
| 5,195,984 A | 3/1993 | Schatz |
| 5,217,495 A | 6/1993 | Kaplan et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,421,955 A | 6/1995 | Lau et al. |
| 5,458,615 A | 10/1995 | Klemm et al. |
| 5,478,349 A | 12/1995 | Nicholas |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,593,412 A | 1/1997 | Martinez et al. |
| 5,607,444 A | 3/1997 | Lam |
| 5,607,463 A | 3/1997 | Schwartz et al. |
| 5,628,775 A | 5/1997 | Jackson et al. |
| 5,634,928 A | 6/1997 | Fischell et al. |
| 5,662,675 A | 9/1997 | Polanskyj Stockert et al. |
| 5,676,654 A | 10/1997 | Ellis et al. |
| 5,683,451 A | 11/1997 | Lenker et al. |
| 5,697,948 A | 12/1997 | Marin et al. |
| 5,702,418 A | 12/1997 | Ravenscroft |
| 5,709,701 A | 1/1998 | Parodi |
| 5,722,669 A | 3/1998 | Shimizu et al. |
| 5,723,003 A | 3/1998 | Winston et al. |
| 5,735,869 A | 4/1998 | Fernandez-Aceytuno |
| 5,749,848 A | 5/1998 | Jang et al. |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,922,020 A | 7/1999 | Klein et al. |
| 5,961,536 A | 10/1999 | Mickley et al. |
| 5,968,069 A | 10/1999 | Dusbabek et al. |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 6,007,517 A | 12/1999 | Anderson |
| 6,022,359 A | 2/2000 | Frantzen |
| 6,033,434 A | 3/2000 | Borghi |
| 6,039,721 A | 3/2000 | Johnson et al. |
| 6,042,589 A | 3/2000 | Marianne |
| 6,056,722 A | 5/2000 | Jayaraman |
| 6,066,155 A | 5/2000 | Amann et al. |
| 6,068,655 A | 5/2000 | Seguin et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,143,016 A | 11/2000 | Bleam et al. |
| 6,165,167 A | 12/2000 | Delaloye |
| 6,179,878 B1 | 1/2001 | Duering |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,241,691 B1 | 6/2001 | Ferrera et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,267,783 B1 | 7/2001 | Letendre et al. |
| 6,273,895 B1 | 8/2001 | Pinchuk et al. |
| 6,273,913 B1 | 8/2001 | Wright et al. |
| 6,312,458 B1 | 11/2001 | Golds |
| 6,315,794 B1 | 11/2001 | Richter |
| 6,319,277 B1 | 11/2001 | Rudnick et al. |
| 6,325,823 B1 | 12/2001 | Horzewski et al. |
| 6,357,104 B1 | 3/2002 | Myers |
| 6,375,676 B1 | 4/2002 | Cox |
| 6,383,171 B1 * | 5/2002 | Gifford et al. ............... 604/508 |
| 6,419,693 B1 | 7/2002 | Fariabi |
| 6,451,025 B1 | 9/2002 | Jervis |
| 6,451,050 B1 | 9/2002 | Rudakov et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,987 B1 | 2/2003 | Plante |
| 6,527,789 B1 | 3/2003 | Lau et al. |
| 6,527,799 B2 | 3/2003 | Shanley |
| 6,555,157 B1 | 4/2003 | Hossainy |
| 6,575,993 B1 | 6/2003 | Yock |
| 6,582,394 B1 | 6/2003 | Reiss et al. |
| 6,592,549 B2 | 7/2003 | Gerdts et al. |

| | | |
|---|---|---|
| 6,599,296 B1 | 7/2003 | Gillick et al. |
| 6,602,282 B1 | 8/2003 | Yan |
| 6,605,062 B1 | 8/2003 | Hurley et al. |
| 6,645,547 B1 | 11/2003 | Shekalim et al. |
| 6,656,212 B2 | 12/2003 | Ravenscroft et al. |
| 6,666,883 B1 | 12/2003 | Seguin et al. |
| 6,679,909 B2 | 1/2004 | McIntosh et al. |
| 6,692,465 B2 | 2/2004 | Kramer |
| 6,702,843 B1 | 3/2004 | Brown |
| 6,712,827 B2 | 3/2004 | Ellis et al. |
| 6,712,845 B2 | 3/2004 | Hossainy |
| 6,723,071 B2 | 4/2004 | Gerdts et al. |
| 6,743,251 B1 | 6/2004 | Eder |
| 6,800,065 B2 | 10/2004 | Duane et al. |
| 6,849,084 B2 | 2/2005 | Rabkin et al. |
| 6,899,728 B1 * | 5/2005 | Phillips et al. .............. 623/1.13 |
| 7,147,656 B2 * | 12/2006 | Andreas et al. ............ 623/1.11 |
| 2001/0020154 A1 | 9/2001 | Bigus et al. |
| 2001/0020181 A1 | 9/2001 | Layne |
| 2001/0044595 A1 | 11/2001 | Reydel et al. |
| 2002/0037358 A1 | 3/2002 | Barry et al. |
| 2002/0107560 A1 | 8/2002 | Richter |
| 2002/0138132 A1 | 9/2002 | Brown |
| 2002/0151955 A1 | 10/2002 | Tran et al. |
| 2002/0156496 A1 | 10/2002 | Chermoni |
| 2002/0177890 A1 | 11/2002 | Lenker |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0176909 A1 | 9/2003 | Kusleika |
| 2003/0199821 A1 | 10/2003 | Gerdts et al. |
| 2003/0225446 A1 | 12/2003 | Hartley |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0098081 A1 | 5/2004 | Landreville et al. |
| 2004/0186551 A1 | 9/2004 | Kao et al. |
| 2004/0215165 A1 | 10/2004 | Coyle et al. |
| 2004/0215312 A1 | 10/2004 | Andreas |
| 2004/0249435 A1 | 12/2004 | Andreas et al. |
| 2005/0010276 A1 | 1/2005 | Acosta et al. |
| 2005/0038505 A1 | 2/2005 | Shuize et al. |
| 2005/0133164 A1 | 6/2005 | Andreas et al. |
| 2005/0149159 A1 | 7/2005 | Andreas et al. |
| 2005/0288763 A1 | 12/2005 | Andreas et al. |
| 2006/0184235 A1 * | 8/2006 | Rivron et al. .............. 623/1.41 |
| 2006/0229700 A1 | 10/2006 | Acosta et al. |
| 2006/0282147 A1 | 12/2006 | Andreas et al. |
| 2006/0282150 A1 | 12/2006 | Olson et al. |
| 2007/0203566 A1 * | 8/2007 | Arbefeuille et al. ........ 623/1.13 |
| 2007/0213803 A1 * | 9/2007 | Kaplan et al. .............. 623/1.11 |

FOREIGN PATENT DOCUMENTS

| | | |
|---|---|---|
| EP | 274129 B1 | 7/1988 |
| EP | 282143 | 9/1988 |
| EP | 0 505 686 | 9/1992 |
| EP | 0 533 960 | 3/1993 |
| EP | 0 596 145 | 5/1997 |
| EP | 947180 | 10/1999 |
| EP | 1266638 B1 | 10/2005 |
| WO | WO 96/33677 | 10/1996 |
| WO | WO 97/46174 | 12/1997 |
| WO | WO 97/48351 | 12/1997 |
| WO | WO 99/01087 A1 | 1/1999 |
| WO | WO 00/15151 A1 | 3/2000 |
| WO | WO 00/32136 A1 | 6/2000 |
| WO | WO 00/41649 A1 | 7/2000 |
| WO | WO 00/50116 | 8/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 03/022178 A1 | 3/2003 |
| WO | WO 03/047651 | 6/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Lefevre et al. "Approach to Coronary Bifurcation Stenting in 2003," Euro PCR, (May 2003) 28 pages total.

"Stent", Definitions from Dictionary.com. Unabridged 9v1.01). Retrieved Sep. 22, 2006, from Dictionary.com website: <http://dictionary.reference.com/search?q=stent>.

Stimpson et al, Parallel Production of Oligonucleotide Arrays Using Membranes and Reagent Jet Printing, BioTechniques 25:886-890 (Nov. 1998).

* cited by examiner

APPARATUS AND METHODS FOR DELIVERY OF BRAIDED PROSTHESES

CROSS-REFERENCES TO RELATED APPLICATIONS

The present application is a continuation of U.S. patent application Ser. No. 10/306,620, filed Nov. 27, 2002, which claims priority to U.S. Provisional Patent Application Ser. No. 60/336,607, filed Dec. 3, 2001, the full disclosures of which are incorporated herein by reference.

BACKGROUND OF THE INVENTION

1. Field of the Invention

The present invention relates generally to medical devices and methods. More particularly, the present invention relates to apparatus and methods for delivering braided and other everting prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or even if survived, cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting, which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that coating stents with anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the successive use of multiple balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature and other body lumens. In particular, it would be desirable to provide stents, delivery systems, and methods for the treatment of disseminated and variable length stenotic regions within the vasculature. For example, it would be desirable to provide a practical method which permits a physician to deliver extended lengths of braided prostheses to blood vessels and other body lumens. At least some of these objectives will be met by the inventions described hereinafter.

2. Description of the Background Art

U.S. Pat. No. 5,755,772 describes a tubular prosthesis and method for its implantation by positioning the prosthesis at a target site, and everting an end session to lock the stent after expansion has been completed; and U.S. Pat. No. 5,769,882 describes conformable tubular prostheses and their placement in blood vessels.

BRIEF SUMMARY OF THE INVENTION

The present invention provides methods and apparatus for the stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable scaffolds which are designed to be intraluminally introduced to a treatment site and expanded in situ to apply a radially outward force against the inner wall of the body lumen at that site. Stents commonly comprise an open lattice structure, typically formed from a malleable or elastic metal.

The stents of the present invention will comprise evertible structures which radially expand upon eversion to assume a non-collapsible diameter which remains in place within the body lumen to support the luminal wall. Typically, the evertible stent structures will comprise braided structures, but other structures, such as counterwound helices, will also be capable of eversion. In some instances, laser cut helical and other patterned metal tubes, particularly those formed from nickel titanium and other shape memory alloys, may be used. Thin wall tubes formed from polymeric materials, such as polyethylene terephthalate (PET), expanded polytetrafluoroethyolene (e PTFE), may also find use, even without patterning.

The braided and other evertible stent structures of the present invention may be formed from metals, including both malleable metals and elastic metals, such as shape memory metals, as well as from polymeric materials. Usually, the braided structures will comprise individual ribbons of the desired material which are interwoven to form a braid so that the braid may be axially elongated to assume a narrow diameter configuration and thereafter be everted to assume a larger diameter configuration. By "evert" it is meant that a leading edge of the prosthesis is turned outwardly and backwardly relative to the narrow diameter portion thereof. In the preferred methods and apparatus of the present invention, as described in more detail below, such eversion will be achieved by initially holding the prosthesis in its narrow diameter configuration with the leading portion everted and fixed to an outer portion of a catheter. This leading portion is referred to as the "fixed end." The remainder of the prosthesis which remains in its narrow diameter configuration is held within a passage or lumen of a delivery catheter, and means are provided for pushing the "advancable end" of the prosthesis which is in the lumen forwardly relative to the fixed end. In this way, the leading edge of the prosthesis moves forward continuously relative to the fixed end as it everts radially outwardly.

The use of such braided and other evertible prostheses provides a number of advantages. For example, the braided structure is highly flexible, particularly in its narrow diameter configuration, allowing the introduction of relatively long stent segments without significantly limiting the ability of the delivery catheter to pass through torturous regions of the vasculature or other body lumens. Additionally, by everting the prosthesis so that its outer portion remains stationary relative to the fixed end (and thus also relative to the delivery catheter), the stent will be able to pass through relatively small body lumens since it advances much like a tractor tread in moving forwardly through the lumen. In the case of vascular treatments, the stents of the present invention will usually be used following other primary interventions, such as angioplasty, atherectomy, aneurysm repair, or the like. It will be possible, however, in certain instances, to deliver the stent without prior intervention because of the ability to advance through tight lesions and to dilate the lesion as it passes therethrough.

Usually, the methods and apparatus of the present invention will be used to deliver a single stent having a predetermined length. In other instances, however, it will be possible to provide a means for severing the stent on the catheter itself. In such cases, the methods and apparatus of the present invention will be capable of delivering variable lengths of stent depending on the nature and extent of the disease being treated. That is, the apparatus will be used to deliver the stent under fluoroscopic or other observation, and after a desired length of stent has been deployed, the deployed length can be severed from the length which remains carried within the delivery catheter.

In one aspect of the present invention, a method for delivering a prosthesis to a body lumen comprises positioning a metallic tubular prosthesis at a target site within the body lumen. The prosthesis is then everted so that an inside surface is exposed radially outwardly and advanced over a length of the wall of the body lumen. Usually, positioning comprises introducing a delivery catheter having a passage which carries the tubular prosthesis at least partly in a radially collapsed configuration. Everting usually comprises pushing the tubular prosthesis from the catheter so that a leading portion of the prosthesis everts and radially expands as it exits the catheter or passage. This is usually accomplished by forwardly advancing a portion of the catheter to push the prosthesis from the catheter. In a preferred aspect of the present invention, an advancable segment of the prosthesis is carried in the passage in the radially collapsed configuration. A fixed end of the prosthesis is held stationary relative to the catheter in a partially everted configuration. Everting then comprises pushing a proximal end (i.e., an end or portion of the prosthesis which is radially collapsed within the delivery catheter) to cause a middle portion of the prosthesis to progressively evert and advance distally relative to the fixed end. In the case of braided prostheses, the braided structure will shorten as the radius expands so that the "advancable" proximal end prosthesis is pushed forward at a rate which is faster than the rate at which the everted prosthesis covers the wall of the body lumen. In preferred embodiments, the prosthesis releases an active substance which inhibits hyperplasia after the prosthesis has been placed in the body lumen.

In another aspect of the present invention, a method for delivering a stent to a blood vessel comprises positioning the stent at a target site within the blood vessel and everting the stent so that an inside surface is exposed radially outwardly and advanced over a length of a wall of the blood vessel. The stent, in turn, inhibits restenosis in the blood vessel.

In another aspect of the present invention, a method for delivering a prosthesis to a body lumen involves positioning a tubular prosthesis at a target site within the body lumen, the tubular prosthesis having a total length. The tubular prosthesis is then everted so that an inside surface is exposed radially outwardly and a desired length of the tubular prosthesis is advanced over a length of a wall of the body lumen, the desired length being less than the total length. The method then includes severing a portion of the tubular prosthesis having the desired length to allow the portion to remain in the body lumen.

In another aspect of the present invention, a method for delivering a prosthesis to a body lumen involves positioning a delivery catheter carrying a tubular prosthesis at a target site within the body lumen, everting the tubular prosthesis so that an inside surface is exposed radially outwardly and advanced over a desired length of a wall of the body lumen, and deploying a portion of the tubular prosthesis having the desired length. A second length of the tubular prosthesis remains carried within the delivery catheter.

In another aspect of the present invention, apparatus for delivering a prosthesis to a body lumen includes a catheter having a passage, a metallic tubular prosthesis carried in the passage at least partially in a radially collapsed configuration, and a slidable member in the catheter for advancing the prosthesis from the passage so that the prosthesis everts and radially expands as it is advanced. In some embodiments, the metallic tubular prosthesis is a shape memory metal. In some embodiments, the metallic tubular prosthesis comprises a braided metal structure. Alternatively, the metallic tubular prosthesis may comprise an open lattice structure.

In yet another embodiment of the present invention, apparatus for delivering a prosthesis to a blood vessel includes a catheter having a passage, a stent carried in the passage at least partially in a radially collapsed configuration, and a slidable member in the catheter for advancing the prosthesis from the passage so that said prosthesis everts and radially expands as it is advanced. The stent is configured to inhibit restenosis in the blood vessel.

In another aspect of the invention, apparatus for delivering a prosthesis to a body lumen includes a catheter having a passage, a tubular prosthesis carried in the passage at least partially in a radially collapsed configuration, a slidable member in the catheter for advancing the prosthesis from the passage so that said prosthesis everts and radially expands as it is advanced, and a severing member in the catheter for severing a portion of the prosthesis to allow the portion to remain in the body lumen while a second portion of the prosthesis remains carried in the catheter.

These and other aspects and embodiments of the present invention will be described in further detail below, with reference to the attached drawing figures.

DETAILED DESCRIPTION OF THE INVENTION

Figure 1:
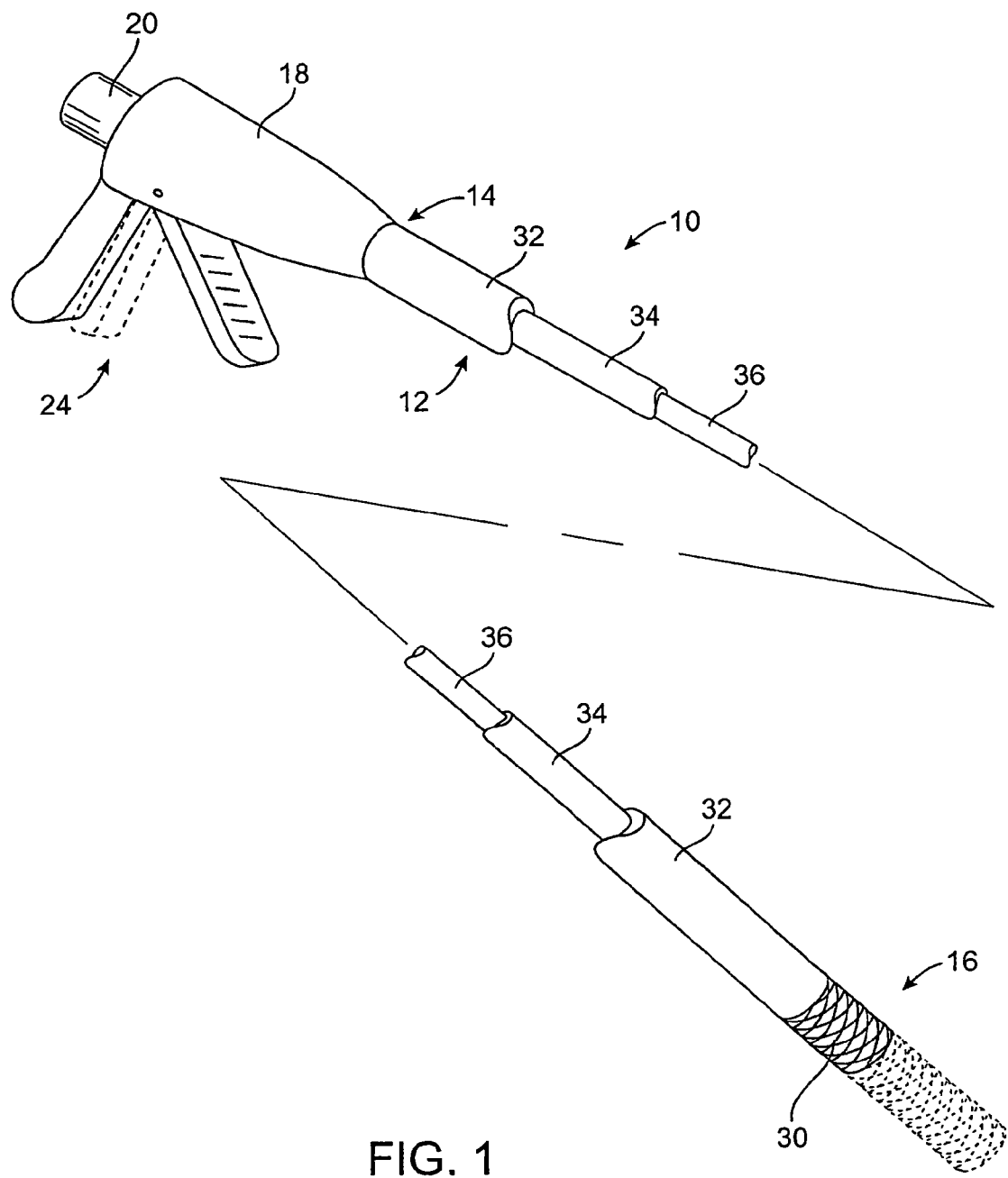
FIG. 1 is a perspective view illustrating a stent delivery catheter constructed in accordance with the principles of the present invention.

Referring now to FIG. 1, the stent delivery catheter 10 comprises a catheter body 12 having a proximal end 14 and a distal end 16. The catheter body 12 is formed from a conventional catheter material, such as a natural or synthetic polymer, such as silicone rubber, polyethylene, polyvinylchloride, polyurethane, polyester, polytetrafluoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French (one French=0.33 mm).

Catheter 10 further comprises a handle 18 at its proximal end 14. The handle has a guidewire port 20 at its distal end as well as a handle grip 24 which is actuable to extend and release evertible prosthesis 30 from the distal end 16. The catheter body 12 comprises an outer tube 32, a middle tube 34 which coaxially and slidably mounted within a lumen of the outer tube 32, and an inner tube 36 which is slidably and coaxially mounted within a lumen of the middle tube 34. Inner tube 36 has a central lumen for receiving a guidewire, as described in detail below.

Figure 2A:
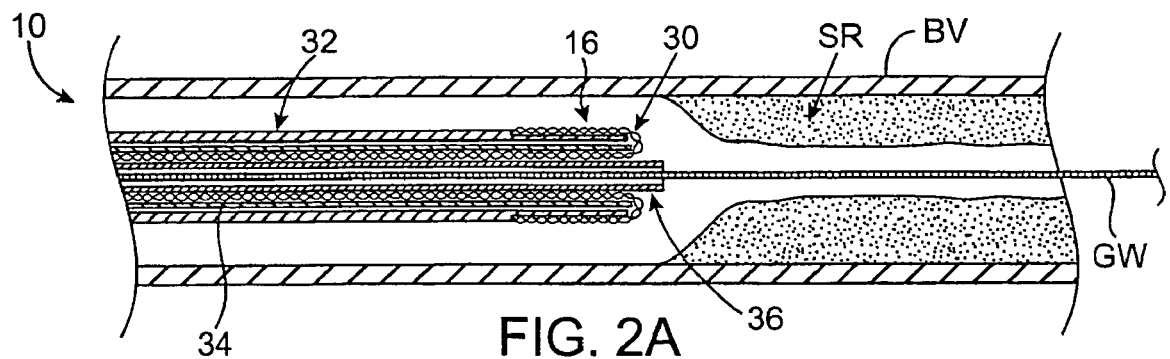
FIGS. 2A-2D illustrate use of the catheter in FIG. 1 for deploying a braided stent within a stenosed region in a blood vessel.

Referring now to FIGS. 2A-2D, delivery of the prosthesis 30 within a stenosed region SR of a blood vessel BV is described. The distal end 16 of the catheter 10 is introduced over a guidewire GW to the stenosed region SR as shown in FIG. 2A.

Figure 2B:
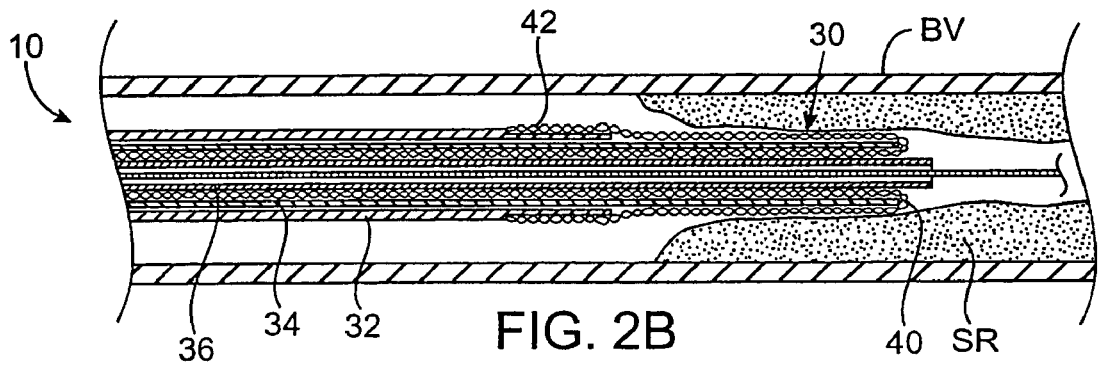

At that point, the prosthesis 30 is advanced forwardly or distally into the stenosed region SR of the blood vessel BV, as shown in FIG. 2B. In particular, both the inner tube 36 and the middle tube 34 are advanced forwardly or distally relative to the outer tube 32. This causes the leading edge 40 of the prosthesis 30 to advance into the stenosed region SR, engaging and partially dilating the lumen wall within this region.

Figure 2C:
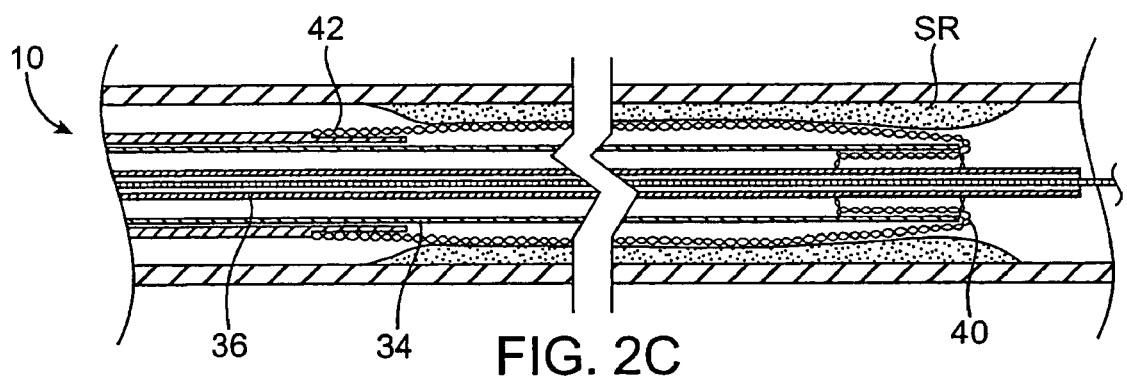

As the inner tube 36 and middle tube 34 are further advanced, as shown in FIG. 2C, the leading edge 40 of the prosthesis advances out through the other end of the stenosed region SR. During this entire deployment, fixed end 42 of the prosthesis has remained on the distal end of the outer tube 32 of the delivery catheter 10.

Figure 2D:
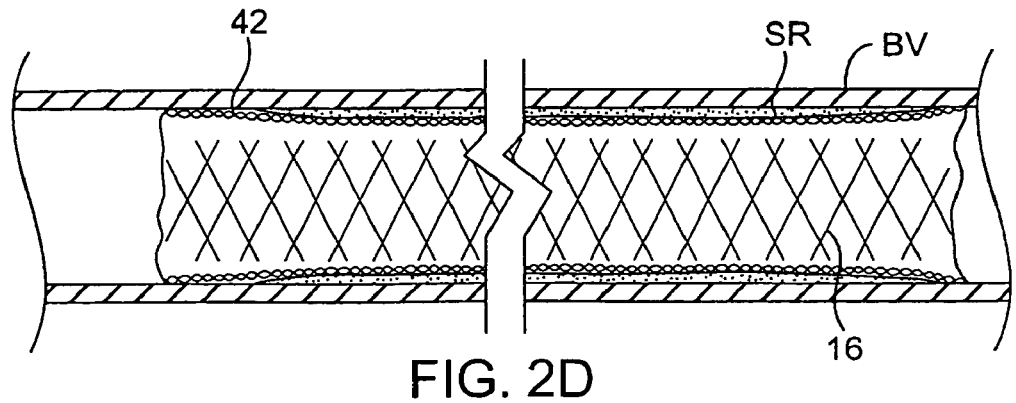

Once the prosthesis 30 is fully deployed, the outer tube 32 would be disengaged from the fixed end 42 of the prosthesis, e.g., by rotating or otherwise separating the catheter from the prosthesis, leaving the prosthesis 30 in place, as shown in FIG. 2D. As can be seen in FIG. 2D, the deployment of the prosthesis 30 has dilated the stenotic region. At this point, if the dilation is insufficient, or further anchoring of the prosthesis 30 is desired, a balloon or other expandable member may be expanded within the prosthesis 30 in a conventional manner. In one embodiment, for example, a balloon may be coupled with the outer tube 32 in such a way as to allow the balloon to be inflated to further anchor the prosthesis 30 in place.

It will be appreciated that the lengths, pitches, adjacent spacings, and the like, of the braided and other elements deployed according to the methods of the present invention can be controlled at the discretion of the treating physician. Thus, the methods and apparatus of the present invention provide useful flexibility for the treating physician to treat extended and disseminated disease in the vasculature and other body lumens.

Although the foregoing invention has been described in some detail by way of illustration and example, for purposes of clarity of understanding, it will be obvious that certain changes and modifications may be practices within the scope of the appended claims.

What is claimed is:

1. A method for delivering a prosthesis to a body lumen, said method comprising:
    positioning a delivery catheter carrying a tubular prosthesis at a target site within the body lumen;
    everting the tubular prosthesis so that an inside surface is exposed radially outwardly and advanced over a desired length of a wall of the body lumen, wherein the prosthesis radially expands into engagement with an inner wall of the body lumen and applies a radially outward force against the inner wall as the prosthesis is everted and advanced; and
    deploying a portion of the tubular prosthesis having the desired length, wherein a second length of the tubular prosthesis remains carried within the delivery catheter.

2. The method of claim 1, further comprising the step of separating a portion of the tubular prosthesis having the desired length from the second length on the delivery catheter.

3. The method of claim 2, wherein the step of separating comprises severing the tubular prosthesis.

4. The method of claim 3, wherein a severing member is disposed on the delivery catheter and adapted to sever the tubular prosthesis.

5. The method of claim 1, further comprising releasing a therapeutic agent from the desired length of the prosthesis after it has been deployed from the delivery catheter.

6. The method of claim 5, wherein the therapeutic agent inhibits hyperplasia.

7. The method of claim 1, wherein positioning comprises carrying the tubular prosthesis in a radially collapsed configuration.

8. The method of claim 1, wherein everting comprises pushing the tubular prosthesis from the catheter.

9. The method of claim 1, further comprising expanding an expandable member within the deployed portion to anchor the deployed portion into the body lumen.

10. The method of claim 9, wherein expanding an expandable member comprises inflating a balloon coupled to the delivery catheter.

11. An apparatus for delivering a prosthesis to a body lumen, said apparatus comprising:
    a catheter having a passage;
    a metallic tubular prosthesis carried in the passage at least partially in a radially collapsed configuration, wherein the metallic tubular prosthesis comprises a braided metal structure; and
    a slidable member in the catheter for advancing the prosthesis from the passage so that said prosthesis everts and radially expands as it is advanced wherein the prosthesis radially expands into engagement with an inner wall of the body lumen and applies a radially outward force against the inner wall as the prosthesis is everted and advanced.

12. The apparatus of claim 11, further comprising a severing member disposed on the delivery catheter adapted to sever the tubular prosthesis thereby allowing a desired length of the severed tubular prosthesis to be released from the delivery catheter while a second portion remains on the delivery catheter.

13. The apparatus of claim 11, wherein the prosthesis carries a therapeutic agent adapted to be released therefrom.

14. The apparatus of claim 13, wherein the therapeutic agent inhibits hyperplasia.

15. The apparatus of claim 11, further comprising an expandable member disposed on the delivery catheter.

16. The apparatus of claim 15, wherein the expandable member comprises a balloon.

17. The apparatus of claim 11, wherein the prosthesis is self-expanding.

18. The apparatus of claim 11, wherein the prosthesis comprises a shape memory alloy.

* * * * *